(12) United States Patent
Tuvim

(10) Patent No.: US 6,348,150 B1
(45) Date of Patent: Feb. 19, 2002

(54) PERMANENTLY RADIALLY COMPRESSED COLUMN

(75) Inventor: Yuri Tuvim, Newton, MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/525,635

(22) Filed: Mar. 14, 2000

Related U.S. Application Data

(63) Continuation-in-part of application No. 09/079,994, filed on May 15, 1998, now abandoned.

(51) Int. Cl.$^7$ .............................................. B01D 15/08
(52) U.S. Cl. ..................................... 210/198.2; 210/656
(58) Field of Search ............................... 210/656, 659, 210/198.2; 95/82; 96/101

(56) References Cited

U.S. PATENT DOCUMENTS

| | | | |
|---|---|---|---|
| 3,941,490 A | 3/1976 | Anton | 401/110 |
| 4,211,658 A | 7/1980 | McDonald et al. | 210/198.2 |
| 4,228,007 A | 10/1980 | Rausch et al. | 210/198.3 |
| 4,250,035 A | 2/1981 | McDonald et al. | 210/198.2 |
| 4,350,595 A | 9/1982 | Gunkel | 210/198.2 |
| 5,089,125 A | 2/1992 | Hart et al. | 210/198.2 |
| 5,220,928 A | 6/1993 | Oddsen et al. | 128/898 |
| 5,540,464 A | 7/1996 | Picha | 210/198.2 |
| 5,866,008 A | 2/1999 | Shalon et al. | 210/198.2 |
| 5,893,971 A | 4/1999 | Shalon et al. | 210/198.2 |
| 6,096,204 A | * 8/2000 | Tuvim | 210/198.2 |

* cited by examiner

Primary Examiner—Ernest G. Therkorn
(74) Attorney, Agent, or Firm—Anthony J. Janiuk

(57) ABSTRACT

An embodiment of the present invention features a chromatographic device. The chromatographic device comprises a body having a cylindrical wall having an exterior diameter. The cylindrical wall is flexible, expanding and contracting in response to radial pressure. The cylindrical wall defines a cavity for holding a chromatographic media. A chromatographic media is retained within said cavity. A spring element surrounds the cylindrical wall, permanently radially compressing said cylindrical wall and opposing the expansion of the wall in response to internal pressure within the cavity. The radial compression prevents the movement of the chromatographic media in the cavity and the opening of channels about the walls of the body.

5 Claims, 4 Drawing Sheets

PERMANENTLY RADIALLY COMPRESSED COLUMN

This application is a continuation in part of U.S. Ser. No. 09/079994, filed May 15, 1998, now abandoned.

FIELD OF THE INVENTION

The present invention relates generally to high performance liquid chromatography (HPLC), and more specifically to HPLC columns.

BACKGROUND OF THE INVENTION

Chromatography is a method by which components of a solution phase are separated by the different affinities exhibited by the components for a stationary phase. Chromatography has become an important tool for measuring the compositions of materials used in the chemical, pharmaceutical, biotechnological, and food industries.

HPLC instruments are comprised of pumps for delivering and moving solvents (the mobile phase), an injector to introduce a sample of interest into the flow of the mobile phase, a tubular column encasement, containing a packed material or bed (the "stationary phase"), and a detector to register the presence and amount of different components in the mobile phase. When the mobile phase is passed through the stationary phase, each component will emerge from the column at a different time because different component in the sample will have different affinities to the packing material. The presence of a particular component in the mobile phase exiting the column can be detected by measuring changes in physical or chemical properties of the eluent. By plotting the detector's signal over time, response "peaks" corresponding to the presence of each of the components of the sample can be observed and recorded.

The resolution between response peaks in a chromatographic analysis or "run" depends, in part, on providing a uniform and reproducible flow of the mobile phase through the stationary phase. Irregularities or changes in the packing material in the column from run to run adversely affect reproducibility of runs, and the reliability of the chromatographic analysis. For example, voids in the packed bed create flow irregularities, leading to overlapping responses or muted response peaks.

The chromatography column encasement is typically stainless steel. This encasement is tightly packed with the stationary phase material by slurry packing, by tapping, or by mechanical ramming.

Within rigid-wall steel columns, voids can occur not only within the packing, but also at the interface between the packing and the encasement wall. This leads to a phenomenon referred to as side or wall channeling, where the mobile phase travels down the wall of the column effectively bypassing the packing or stationary phase. Such side channeling decreases the reliability and reproducibility of the chromatographic peaks, and hence their analytical value.

While a tightly packed bed is less prone to deterioration, degradation still occurs no matter how well the packing is initially done. Vibration during shipping and handling, temperature fluctuations, and/or mobile phase changes can also cause the formation of voids.

Columns have been made with a plastic encasement containing the packing materials. However, such plastic columns tend to have poor performance. Under the pressure of a mobile phase, the plastic expands and voids are formed between the packing material and the plastic tube wall resulting in the loss of performance.

A typical plastic column is packed such that the chromatographic medium is under initial radial compression. This radial compression is provided by the plastic wall of the column. When used, the column is further radially compressed under the influence of gas or liquid. To achieve this the column is placed in a pressure vessel and subjected to external compression pressures up to 3000 psi. This approach requires the chromatography bench to be equipped with an appropriately sized apparatus to provide compression of the column. Such apparatus adds to the expense of the standard chromatography work station.

A simple mechanism to impart and maintain radial compression on chromatography columns is desired.

SUMMARY OF THE INVENTION

The present invention provides a substantially permanently radially compressed chromatography device which does not require additional compression on the chromatography bench.

One embodiment of the present invention features a chromatographic device. The chromatographic device comprises a body having a cylindrical wall having an exterior diameter. The cylindrical wall is flexible, expanding and contracting in response to radial pressure. The cylindrical wall defines a cavity for holding a chromatographic media. A chromatographic media is retained within the cavity. A spring element surrounds the cylindrical wall, permanently radially compressing the cylindrical wall and opposing the expansion of the wall in response to internal pressure within the cavity. The radial compression prevents the movement of the chromatographic media in the column and the opening of channels about the walls of the column.

Preferably, the spring element is a spiral spring having spirals. The spirals define a spring cylinder having an internal diameter less than the exterior diameter of the cylindrical wall in a relaxed first position, and defining an internal diameter greater than the exterior diameter of the cylindrical wall in an unwound second position. The spiral spring surrounds the cylindrical wall of body in an intermediate third position providing radial compression on said cylindrical wall as the spiral spring is urged to the relaxed first position.

According to the invention, a substantially permanently radially compressed chromatographic column is provided having a flexible-walled encasement containing chromatographic media. A spring element is disposed surrounding the encasement and provides radial compression of the column.

The present invention features increased radial compression. In addition, the natural resiliency of the flexible walls of the encasement prevents the formation of voids during handling and shipping. The present invention advantageously provides for permanent radial compression, such that channeling and other factors which lead to performance degradation during the use of the chromatography apparatus are substantially diminished.

The present invention also advantageously provides for a low cost alternative to the prior art, dispensing with the need for expensive radial compression apparatus on the chromatography bench.

Further advantageously, the present invention provides a chromatographic column with an enhanced usable life span compared with the prior art.

BRIEF DESCRIPTION OF THE DRAWINGS

The foregoing and other features and advantages of the present innovation will be more fully understood from the following detailed description of an illustrative embodiment, taken in conjunction with the accompanying drawing in which.

DETAILED DESCRIPTION OF AN ILLUSTRATIVE EMBODIMENT

The present invention will be described herein with reference to an illustrative embodiment of a permanently radially compressed chromatographic device in the form of a cartridge or column.

Figure 1:
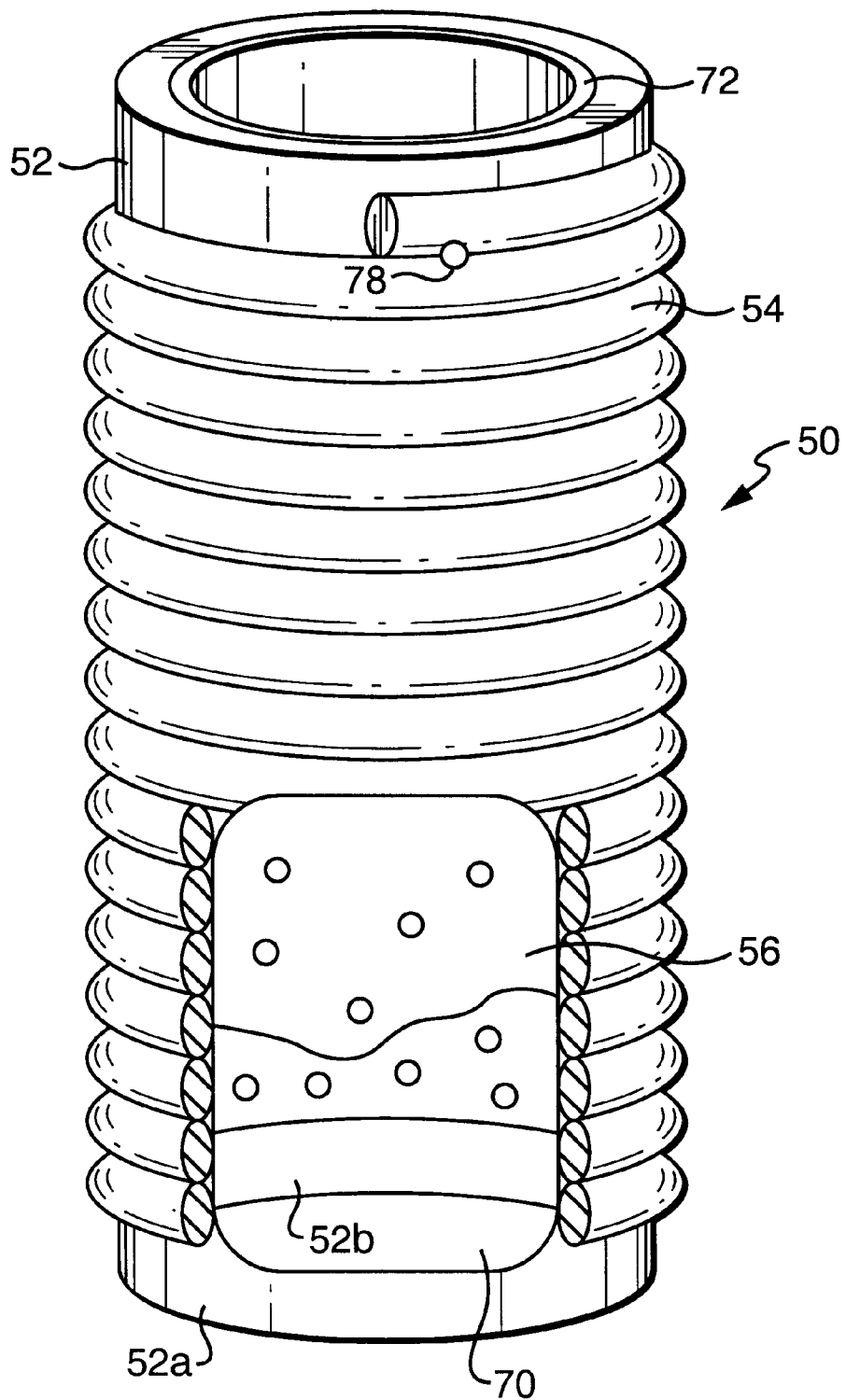
FIG. 1 depicts one aspect of a column (with cut away view) according to the present invention.

Turning now to FIG. 1, one aspect of a chromatographic column according to the present invention is illustrated. The chromatographic column, generally designated by the numeral 50, comprises the following major parts: a body or column encasement 52, a spring element in the form of a spiral spring 54, and a stationary phase 56.

Encasement 52 is a plastic tube having an exterior wall 52a and interior wall 52b. The interior wall 52b defines a chamber for containing a packing material 56. A typical 40 mm by 10 mm cartridge will have a total height of approximately 5.46 inches. The inner chamber, defined by inner wall 52b has a diameter of approximately 1.57 inches. The exterior wall 52a has a diameter of approximately 1.97 inches. Typical plastics for encasements are PP or HDPE.

Figure 2:
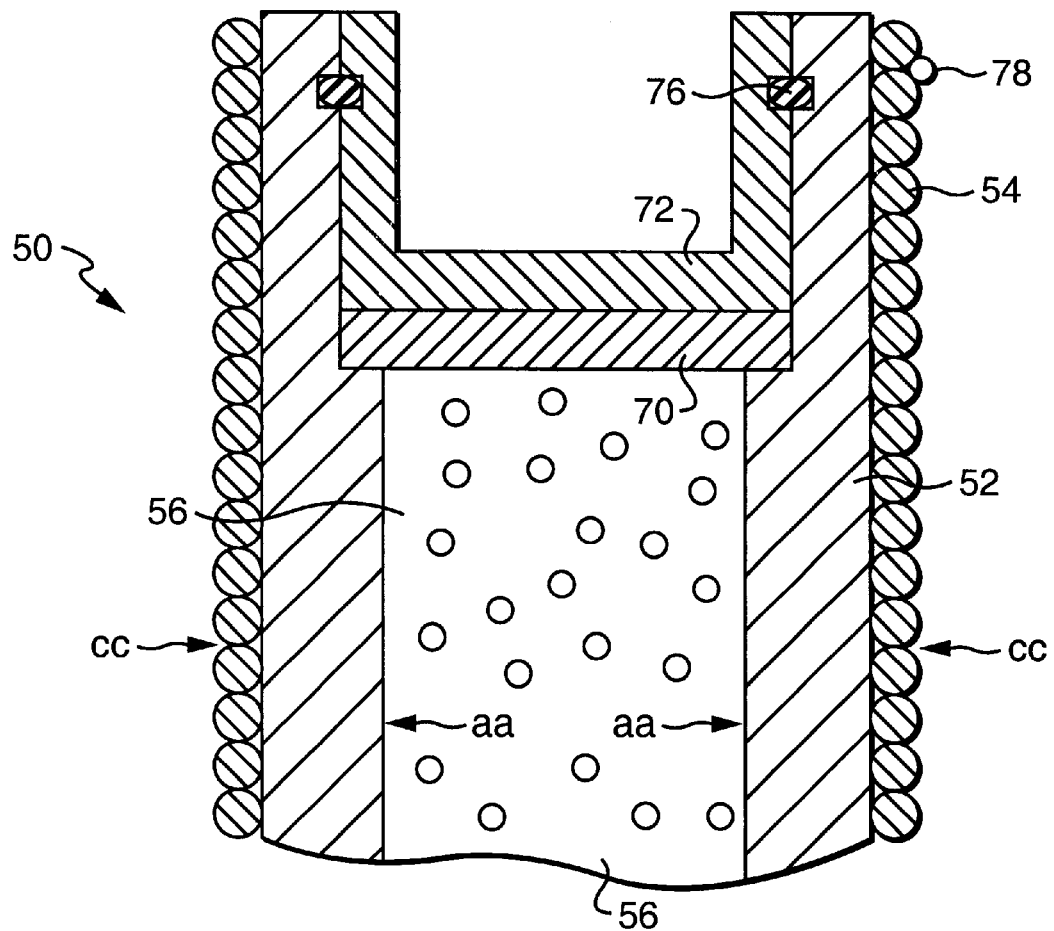
FIG. 2 depicts the column of FIG. 1 in cross section.

Encasement 52 is packed with the stationary phase 56. The packing of stationary phase 56 forces the walls of encasement 52 radially outward as best seen in FIG. 2 and arrows aa.

Typically, the stationary phase is comprised of particles that are packed under pressure of approximately 1,000 to 10,000 psi. For purposes of clarity, the stationary phase is depicted as a solid mass.

Spiral spring 54 surrounds the cylindrical exterior wall 52a, permanently radially compressing the cylindrical wall and opposing the expansion of the wall in response to internal pressure within the cavity. The radial compression prevents the movement of the chromatographic media or stationary phase 56 in the column and the opening of channels about the interior walls 52b of the column 50.

Figure 3:
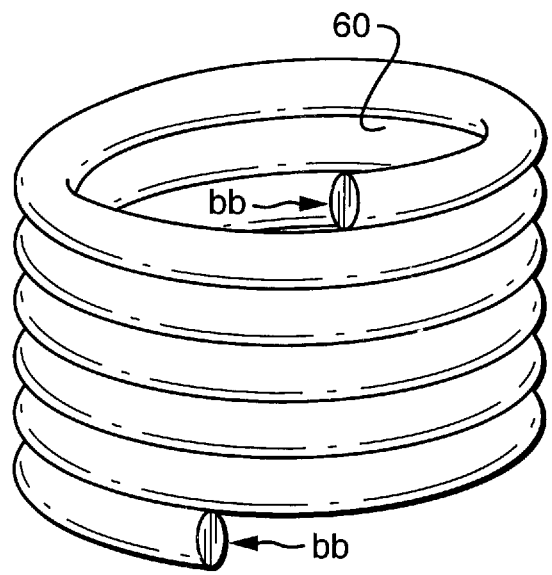
FIG. 3 depicts the spring element of the column of FIG. 1.
Figure 4:
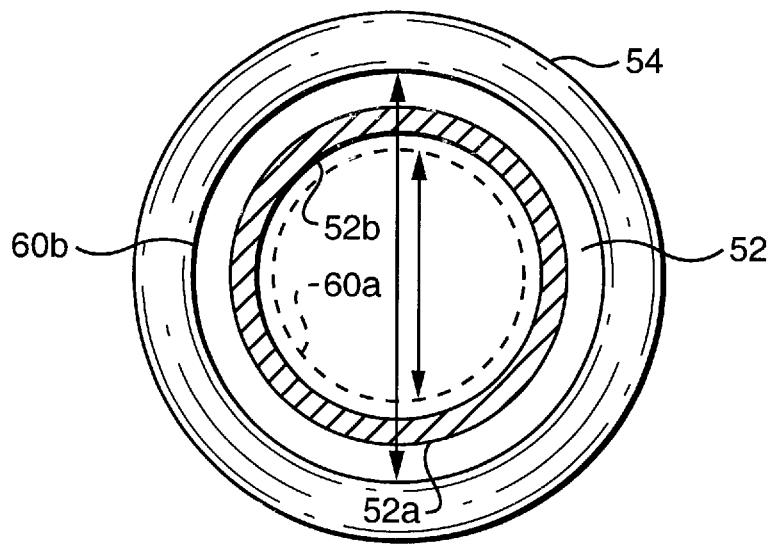
FIG. 4 depicts a top view of the column of FIG. 1 being made according to the present invention; and, FIG. 5 depicts a sleeve device embodying features of the present invention.

The spiral spring 54 has spirals which define a spiral cylinder 60 as best seen in FIGS. 3 and 4. The spiral cylinder 60 has two positions. In a first position, where spiral spring 54 is substantially relaxed, the spiral cylinder 60 has an internal diameter 60a less than the exterior diameter of the cylindrical wall 52a of the encasement 52, as best seen in FIG. 4. For example, where the outside diameter of the encasement may be approximately 1.97 inches, the spiral cylinder 60 has a diameter in a first relaxed position of 1.75 inches. In a second position, the spiral spring 54 is unwound and under tension as depicted by arrows bb in FIG. 3. In this second position, the spiral cylinder 60 has an internal diameter 60b greater than the exterior diameter of the cylindrical wall 52a of the encasement 52, again, as best seen in FIG. 4. The spiral spring 54, tightly surrounding the cylindrical wall 52a of the encasement 52, in a partially unwound third position. The third position is between the first position 60a and the second position 60b. In this third position, the spiral spring 54 provides radial compression on the cylindrical wall 52a as the spiral cylinder 60 is urged to the relaxed first position 60a.

Column 50 has a frit 70 as best seen in FIGS. 1 and 2. The frit 70 serves to retain the stationary phase 56 within the encasement 52. An end cap 72 retains the frit 70 within encasement 56. A seal 76 interposed between the end cap 74 and the inner wall 52a of the encasement 52 prevents fluid leaks. The inward radial pressure of the spring is weakest at the end of the spiral. To prevent the spiral spring 54 from allowing the ends of the encasement to radially expand under pressure, spring 54 is provided with a laser weld, or other securement 78. The weld or other securement 78 substantially prevents spring 54 from unwinding under internal pressure created by the flow of mobile phase through the packed bed.

Figure 5:
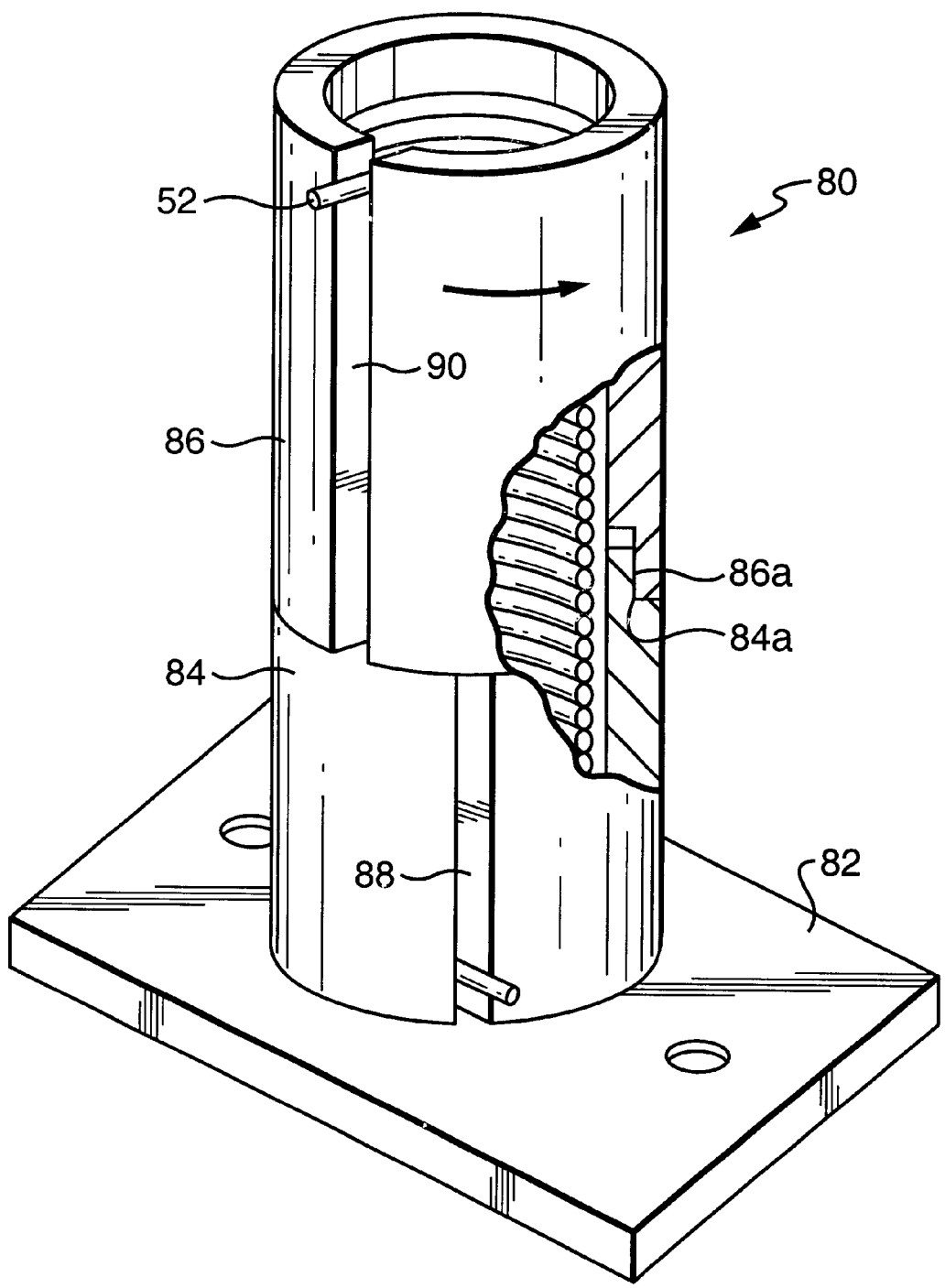

To facilitate the making of the column 50, a further embodiment of the present invention features an unwinding device, generally designated by the numeral 80 in FIG. 5. Unwinding device 80 is comprised of a base 82, a first sleeve 84 and a second sleeve 86. First sleeve 84 and second sleeve 86 are cylinders with an internal diameter greater than the spiral cylinder diameter in the unwound second position. Each sleeve has means to receive an end of the spiral spring 54 such as clips, clamps, or openings. Preferably, spiral spring 54 has outwardly directed ends which cooperate with slots 88 and 90 in the first and second sleeve respectively. The first and second sleeve 84 and 86 are linked to allow rotation by a cooperating interfitting rims 84a and 86a. The interfitting rims 84a and 86a of the first and second sleeves 84 and 86 allow the first and second sleeve separate to allow removal of the encasement 52 from the unwinding device 80. First sleeve 84 is secured to base 82 to allow ease of handing and stability of the unwinding device 80.

A spiral spring 54 is received in the unwinding device 80 with the ends of the spring in slots 88 and 90. Rotation of the second sleeve 86 with respect to first sleeve 84, unwind spiral spring 54. In the unwound second position, spiral spring receives an encasement 52. With the encasement 52 in place, the torque placed on first sleeve 84 and second sleeve 86 is released. The second sleeve 86 is lifted from the encasement 52, spiral spring 54 and first sleeve 84. Encasement 52 can then be removed for first sleeve 84 as one of the ends of spiral spring 54 slides through slot 88.

To make a cartridge of the present invention, encasement 52 receives a frit 70, end cap 72 and seal 76. A stationary phase is placed in the encasement and the opposite end of the encasement 52 receives a second frit 70, end cap 72 and seal.

Spiral spring 54 is placed in unwinding device 80, and spiral spring 54 is partially unwound, by urging or twisting the ends of the spirals in the direction of arrows bb. The partial unwinding urges the spiral cylindrical wall 60 from a relaxed first position 60a with a small diameter to the second position 60b with a larger diameter 60b. Encasement 52 is placed inside the cylinder defined by the spirals of the spiral spring element 54. The unwinding torque is removed and the spiral spring 54 coils back, urged to the relaxed first position 60a. The spiral spring 54 is prevented from fully assuming the first position 60a. The exterior wall 52a of the encasement 52 receives the spring 54. The spiral spring 54 squeezes and compresses the encasement 52 with a substantially constant radial force as represent by arrows cc as best seen in FIG. 2.

The encasement 52 wit the spiral spring 54 is removed from the unwinding device by first removing the second sleeve 86. Next, the encasement 52 and spiral spring 52 is removed from the first sleeve 84. The projecting ends of the spiral spring 54 are preferably trimmed.

In the alternative, the stationary phase 56, frits 70, end caps 72 and seals 76 can be placed in the encasement 52 after the encasement 52 is fitted with the spiral spring 54.

Spiral spring 54 is welded at 78 to secure the end of the spring to prevent expansion and lock the diameter of the spring in place.

The present invention advantageously supplements the natural resiliency of the flexible walls of a chromatographic cartridge with that of a spring thus maintaining the cartridge under increased radial compression. This offers distinct advantages over metal columns, which cannot be compressed and also over the prior art flexible wall cartridges. The inherent compression of prior art flexible wall cartridges is not sufficient to prevent the formation of voids because the strength of the plastic is insufficient to withstand the internal pressure, and requires additional apparatus to radially compress the cartridge when running a chromatographic analysis. The present invention, by permanently radially compressing the cartridge with forces sufficient to maintain uniformity of the separation medium dispenses with numerous problems inherent in the prior art design.

Further, the present invention can be manufactured inexpensively. The use of the present invention is less expensive because complicated apparatus for radially compressing the cartridge composed of a source of pressure, a chamber, tubing, check valve(s), gauge(s), etc. is replaced by a simple device that holds the cartridge between two end connectors.

Although the illustrative embodiment has been described with reference to a spiral spring, other springs may be used, including ribbon springs and square wire spiral springs. Further, the spring may be fashioned of any known material exhibiting the necessary strength, for example, composites. Further, although the invention has been shown incorporating a cartridge having a seal 76 proximate to the end of the cartridge body, the cartridge can be modified, placing the seal closer to the frit 70. In this alternative implementation, the weld 78 might be eliminated. Still further, multiple welds might be implemented in any embodiment, or the spring might alternately be maintained by other mechanical fixing means.

Although the invention has been shown and described with respect to exemplary embodiments thereof, various other changes, additions and omissions in the form and detail thereof may be made therein without departing from the spirit and scope of the invention.

What is claimed is:

1. A chromatographic device comprising:
   (a.) a body having a cylindrical wall having an internal diameter and external diameter, said cylindrical wall flexible, expanding and contracting in response to radial pressure, said cylindrical wall defines a cavity for holding a chromatographic media;
   (b.) a chromatographic media retained within said cavity; and,
   (c.) a spring element surrounding said cylindrical wall, permanently radially compressing said cylindrical wall about the external diameter and opposing the expansion of the wall in response to internal pressure within said cavity, said radial compression preventing the movement of the chromatographic media in the cavity and the opening of channels about the walls of the cavity.

2. The chromatographic device of claim 1, wherein said spring element surrounding the encasement comprises a spiral spring.

3. The chromatographic device of claim 1, wherein said spring element is a spiral spring having spirals which define a cylinder having an internal diameter less than the exterior diameter of said cylindrical wall in a relaxed first position, and defining an internal diameter greater than the exterior diameter of said cylindrical wall in an unwound second position, said spiral spring surrounding said cylindrical wall in a intermediate position providing radial compression on said cylindrical wall as said spiral spring is urged to said relaxed first position.

4. The chromatographic device of claim 3, wherein said spring is mechanically retained to itself to prevent expansion and to retain the spring on said body.

5. The chromatographic device of claim 4, wherein said spring is welded to itself.

\* \* \* \* \*